United States Patent
Mehrpouyan et al.

(10) Patent No.: US 9,347,863 B2
(45) Date of Patent: May 24, 2016

(54) PHOSPHOROTHIOATE OLIGONUCLEOTIDE-LABELING OF WHITE BLOOD CELLS

(71) Applicant: BECTON, DICKINSON AND COMPANY, Franklin Lakes, NJ (US)

(72) Inventors: Majid Mehrpouyan, Gilroy, CA (US); Marybeth Sharkey, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 106 days.

(21) Appl. No.: 14/364,055

(22) PCT Filed: Dec. 17, 2012

(86) PCT No.: PCT/US2012/070186
§ 371 (c)(1),
(2) Date: Jun. 9, 2014

(87) PCT Pub. No.: WO2013/096229
PCT Pub. Date: Jun. 27, 2013

(65) Prior Publication Data
US 2015/0087005 A1    Mar. 26, 2015

Related U.S. Application Data

(60) Provisional application No. 61/577,502, filed on Dec. 19, 2011.

(51) Int. Cl.
| G01N 1/44 | (2006.01) |
| G01N 33/49 | (2006.01) |
| C07K 16/28 | (2006.01) |
| G01N 33/569 | (2006.01) |
| G01N 33/58 | (2006.01) |

(52) U.S. Cl.
CPC .............. *G01N 1/44* (2013.01); *C07K 16/2803* (2013.01); *G01N 33/491* (2013.01); *G01N 33/56972* (2013.01); *G01N 33/582* (2013.01); *G01N 2333/70596* (2013.01)

(58) Field of Classification Search
CPC ..... G01N 1/44; G01N 33/491; G01N 33/582; G01N 33/56972; G01N 2333/70596; C07K 16/2803
See application file for complete search history.

(56) References Cited

U.S. PATENT DOCUMENTS

| 5,776,709 A | 7/1998 | Jackson et al. |
| 6,153,113 A | 11/2000 | Goodrich et al. |
| 7,338,762 B2 | 3/2008 | Gorenstein et al. |

(Continued)

OTHER PUBLICATIONS

Liang et al. The Role of Cell Surface Receptors in the Activation of Human B Cells by Phosphorothionate Oligonucleotides. The Journal of Immunology 165: 1438-1445 (2000).*

(Continued)

*Primary Examiner* — Gail R Gabel
(74) *Attorney, Agent, or Firm* — Bret E. Field; Bozicevic, Field & Francis LLP

(57) ABSTRACT

The present invention provides labeling and capture reagents that comprise phosphorothioate oligonucleotides (PS-ODN). The PS-ODN bind to all white blood cells (leukocytes) in an indiscriminative fashion and enable the labeling, capture, or concentration of leukocytes in a manner that preserves the antigenic integrity of the cells. Methods for the use of phosphorothioate oligonucleotides are provided.

20 Claims, 7 Drawing Sheets

PS-ODN#2 (unlabeled)

PS-ODN#2 labeled with FITC at cytosine bases

(56) References Cited

U.S. PATENT DOCUMENTS

| | | | |
|---|---|---|---|
| 7,410,975 B2* | 8/2008 | Lipford | A61K 31/122 514/266.2 |
| 2006/0121023 A1* | 6/2006 | Weiner | G01N 33/5306 424/133.1 |

OTHER PUBLICATIONS

Jarhsdorfer et al. Phosphorothioate oligonucleotides block nonspecific binding of Cy5 conjugates to monocytes. Journal of Immunological Methods 297: 259-263 (2005).*

Iversen et al. "Binding of Antisense Phosphorothioate Oligonucleotides to Murine Lymphocytes is Lineage Specific and Inducible", Antisense Research and Development, vol. 2, No. 3, Sep. 21, 1992, pp. 223-233.

Liang et al. "The Role of Cell Surface Receptors in the Activation of Human B Cells by Phosphorothioate Oligonucleotides", The Journal of Immunology, vol. 165, No. 3, Aug. 1, 2000, pp. 1438-1445.

TarrasÓn et al. "Digoxigenin-Labeled Phosphorothioate Oligonucleotides: A New Tool for the Study of Cellular Uptake", Antisense Research and Development, vol. 5, Jan. 1, 1995, pp. 193-201.

Mcafee et al. "Technique of Leukocyte Harvesting and Labeling: Problems and Perspectives", Seminars in Nuclear Medicine, vol. 14, No. 2, Apr. 1, 1984, pp. 83-106.

De Guise et al. "Monoclonal antibodies to lymphocyte surface antigens for cetacean homologues to CD2, CD19 and CD21", Veterinary Immunology and Immunopathology, vol. 84, No. 3-4, Jan. 15, 2002, pp. 209-221.

Jahrsdorfer et al. "Phosphorothyoate oligodeoxynucleotides block nonspecific binding of Cy5 conjugates to monocytes", Journal of Immunological Methods, vol. 297, 2005, pp. 259-263.

Van Vugt et al. "Binding of PE-CY5 conjugates to the human high-affinity receptor for IgG (CD64) [letter; comment]", Blood, vol. 88, 1996, pp. 2358-2361.

Zhao et al. "Site of Chemical Modifications in CpG Containing Phosphorothioate Oligodeoxynucleotide Modulates Its Immunostimulatory Activity", Bioorganic & Medicinal Chemistry Letters, vol. 9, 1999, pp. 3453-3458.

* cited by examiner

Figure 1
Labeling cytosine bases in PS-ODN with FITC.

Figure 2
Labeling the 5' end of PS-ODN with FITC.

Figure 5
Staining cells with FITC-PS-ODN#2 and CD19-PE-Cy7

Figure 6
Staining cells with FITC-PS-ODN#5 and CD19-PE-Cy7

Figure 7

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tcgtcgtttt gtcgttttgt cgtt                                          24

<210> SEQ ID NO 2
<211> LENGTH: 24
```

```
<212> TYPE: DNA
<213> ORGANISM: Artificial sequence
<220> FEATURE:
<223> OTHER INFORMATION: Synthetic oligonucleotide

<400> SEQUENCE: 2
tgctgctttt gtgcttttgt gctt                                      24

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
gggggacgat cgtcggggggg                                          20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
gggggagcat gctgggggggg                                          20

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
tcgtcgtttt cggcgcgcgc c                                         21
```

PHOSPHOROTHIOATE OLIGONUCLEOTIDE-LABELING OF WHITE BLOOD CELLS

CROSS-REFERENCE TO RELATED APPLICATIONS

Pursuant to 35 U.S.C. §119 (e) this application claims priority to the filing date of U.S. Provisional Patent Application Ser. No. 61/577,502 filed Dec. 19, 2011; the disclosure of which application is herein incorporated by reference.

BACKGROUND OF THE INVENTION

The present invention relates to the field of cell analysis. Phosphorothioate oligonucleotides (PS-ODN) are a variant of normal DNA in which one of the non-bridging oxygens is replaced by a sulfur atom.

DESCRIPTION OF RELATED ART

Labeling of white blood cells (WBC), or leukocytes (also spelled "leucocytes"), using a binding compound that binds to all white blood cells is useful both in the analysis of cells by, for example, flow cytometry and microscopy, and in the enrichment or separation of white blood cells from, for example, whole blood. Typically, an antibody is used that specifically binds to a cell surface protein that is expressed by all WBC, such as CD45. CD45 (also known as leukocyte common antigen, GP180, or T200) is found on all hematopoietic cells except those of red cell origin.

For cell analysis, anti-CD45 antibody is labeled with a detectable label, e.g., a fluorescent dye, to facilitate detection of the cells. The antibodies are mixed with the sample containing white blood cells, such that the cells become fluorescently labeled through the binding of the antibody to the cell-surface marker. The labeled cells then can be identified and enumerated using an instrument, such as a flow cytometer or a microscope. Dye-labled anti-CD45 antibodies are commercially available from, for example, BD Biosciences (San Jose, Calif.). For enrichment or separation, the anti-CD45 antibody typically is conjugated to a solid surface, such as the surface of magnetic particles. The antibody-conjugated magnetic particles are mixed with the sample containing white blood cells, such that the cells become magnetically labeled through the binding of the antibody to the cell-surface marker. The magnetically labeled cells can be concentrated by placing the sample in a magnetic field.

Typically, the magnetically labeled cells are washed to separate the cells from the sample. Magnetic nanoparticles conjugated to anti-CD45 antibodies are commercially available from, for example, BD Biosciences (San Jose, Calif.). B. Jahrsdorfer, et al. 2005. J. Immun Method. 297: 259-263 describe a study that demonstrates that phosphorothioate oligodeoxynucleotides (PS-ODN) suppress non-specific binding of Cy5-based monoclonal antibody conjugates, including those containing PE-Cy5 and Cy5 alone, to monocytes and macrophages. This suppression appears to be mediated by PS-ODN binding to CD64, thereby blocking the binding of Cy5 to this receptor. They conclude that PS-ODN can be used as a reagent to prevent nonspecific binding of Cy5-based immune-conjugates to monocytes in flow cytometry assays. E. R. Kandimalla, et al. 2001. Bioorg. Med. Chem. 9: 807-813, describe CpG oligonucleotides and their synthesis. CpG oligonucleotides are used as stimulatory molecules for the activation of certain cells of the immune system.

BRIEF SUMMARY OF THE INVENTION

The present invention is based on the unexpected discovery by the inventors that phosphorothioate oligonucleotides (PS-ODN) bind to all white blood cells (leukocytes) in an indiscriminative fashion, and that the binding of PS-ODN to leukocytes is sufficiently strong such that PS-ODN can be used either as cell labeling reagents or for use as cell separation reagents.

In another aspect, the present invention provides methods of fluorescently labeling leukocytes in a manner that maintains the surface and/or antigenic integrity of the cell. In some embodiments the method comprises the steps of adding fluorescent dye-PS-ODN conjugates of the present invention to a fluid containing leukocytes with the under conditions such that the fluorescent dye-PS-ODN conjugates become bound to leukocytes. The fluorescent dye-PS-ODN conjugates can then be optically analyzed using any of the well-known instruments and techniques, such as by flow cytometry or microscopy. In some embodiments optical analysis may further comprise binding the labeled cells to any known monocyte immuno-conjugates.

In one aspect, the present invention provides a method for labeling leukocytes, comprising the step of adding a conjugated phosphorothioate oligonucleotide to a fluid containing leukocytes under conditions such that the conjugated phosphorothioate oligonucleotide becomes bound to the leukocytes. In some embodiments the method may further comprise adding an immuno-conjugate to the fluid under conditions such that the immune-conjugate becomes bound to the leucocytes. The conjugated phosphorothioate oligonucleotide may be conjugated to a labeling reagent such as a fluorescent dye or capture reagent. In some embodiments the capture reagent is magnetic. In some embodiments the method may further comprise placing the fluid in a magnetic field such that leukocytes bound to magnetic capture reagents conjugated to phosphorothioate oligonucleotide are concentrated. In some embodiments the methods of this invention further comprises adding an immuno-conjugate to the concentrated leucocytes under conditions such that the immune-conjugate becomes bound to the leucocytes. The immuno-conjugate may be an antibody specific for any leukocyte type such as an anti-CD19 antibody.

In one aspect, the present invention provides labeled reagents for the labeling of leukocytes. The labeled reagents may comprise a phosphorothioate oligonucleotide (PS-ODN) that is conjugated to a detectable label. In preferred embodiments, the detectable label is a fluorescent dye. The detectable label dye may be conjugated directly to the PS-ODN or, preferably, is conjugated to the PS-ODN through a linker. P. S. Miller and Cushman, C. D. (1992). Bioconj. Chem. 3: 74-79, describe the chemical modification of cystine residues. Alternatively, the detectable label may be bound to the PS-ODN through the binding of two members of a binding pair, one conjugated to the PS-ODN and the other conjugated to the detectable label.

In another aspect, the present invention provides capture reagents for binding leukocytes to a solid surface. The capture reagents comprise a phosphorothioate oligonucleotide (PS-ODN) that is conjugated to a solid surface. A wide range of solid surfaces can be used in the present invention, including, for example, beads, plates, slides, columns, microfluidic channels, etc.

The solid surface may be conjugated directly to the PS-ODN or, preferably, is conjugated to the PS-ODN through a linker. Alternatively, the solid surface may be bound to the PS-ODN through the binding of two members of a binding pair, one conjugated to the PS-ODN and the other conjugated to the solid surface.

In some embodiments, the PS-ODN is bound to a detection moiety or solid surface through a cleavable linker. Linkers that can be cleaved by either chemical or enzymatic means are well known in the art. For example, an oligonucleotide linker containing an enzyme cleavage site may be added to the PS-ODN during synthesis. In preferred embodiments, a cleavable linker is created by adding an oligonucleotide "tag" or extension to the PS-ODN during synthesis. The extension may contain an enzyme cleavage site. In some embodiments, wherein the detection moiety or solid surface is bound to the PS-ODN through the binding of two members of a binding pair, one conjugated to the PS-ODN and the other conjugated to the detection moiety or solid surface, the bond may be broken by competitive binding to an excess of one or the other member of the binding pair.

PS-ODN suitable for use in the present invention may be any length, such as between 2 and 100 nucleotides in length, preferably are between 15 and 30, more preferably between 15 and 25, nucleotides in length. In a preferred embodiment, the PS-ODN comprises a sequence selected from ODN#1, ODN#2, ODN#3, ODN#4, and ODN#5, shown in Table 1, below. In more preferred embodiments, the PS-ODN is selected from ODN#1, ODN#2, ODN#3, ODN#4, and ODN#5, shown in Table 1, below. More preferably, the PS-ODN is either ODN#2 or ODN#5.

Also comprehended by this disclosure are compositions and kits which include a PS-ODN labeled with either a detectable label or a magnetic label, as described herein.

BRIEF DESCRIPTION OF THE SEVERAL VIEWS OF THE DRAWINGS

FIG. 4 shows data demonstrating the binding of PS-ODN#5 to total white blood cells.

Leukocyte subpopulations of granulocytes, monocytes, and lymphocytes are labeled as G, M and L, respectively.

DETAILED DESCRIPTION OF THE INVENTION

In order that the invention herein described may be fully understood, a number of terms are explicitly defined, below. Terms not explicitly defined are intended to have their usual meaning in the fields of microscopy, cytometry, immunology, and biology, in general. All reference cited herein, both supra and infra, are incorporated herein by reference.

The terms, white blood cells, leukocytes, and leucocytes are used interchangeably herein. By "whole blood" is intended a fluid blood sample as drawn in the presence of an anticoagulant from a mammal and substantially unfractionated thereafter.

A "labeling reagent", as used herein, refers to any reagent that comprises a detectable moiety and is capable of binding to an analyte of interest, e.g., a cell, to obtain a labeled analyte. Typically, a detection reaction of the present invention will comprise a PS-ODN conjugated to a detectable label, such as a fluorescent dye. The binding of a dye-bound PS-ODN to leukocytes results in the leukocytes becoming labeled with the dye.

A "capture reagent", as used herein, refers to any reagent that capable of binding to an analyte of interest, e.g., a cell, and that is either bound to, or is capable of binding to, a solid surface. Typically, a detection reaction of the present invention will comprise a PS-ODN conjugated to a solid surface. The binding of a dye-bound PS-ODN to leukocytes results in the leukocytes becoming immobilized on the solid surface.

The present invention provides labeling and capture reagents that comprise phosphorothioate oligonucleotides (PS-ODN). The PS-ODN of this invention may bind to all white blood cells (leukocytes) in an indiscriminative fashion, and enable the labeling, capture, or concentration of leukocytes in a manner that preserves the antigenic integrity of the cells. Particles or dyes may be conjugated directly to the PS-ODN or, preferably, is conjugated to the PS-ODN through a linker. In one aspect, the present invention provides methods of capturing, enriching, or concentrating leukocytes, comprising the steps of contacting a fluid containing leukocytes with PS-ODN bound to a solid surface under conditions such that the leukocytes become bound to the PS-ODN and are thereby captured by the solid surface. Preferably, the surface captured leukocytes are separated from the fluid for further analysis or use. Further analysis or use may comprise contacting the captured leukocytes with monocyte immuno-conjugates. The use of surface-bound capture reagents, in general, to capture, enrich, or concentrate cells is well known in the art. The capture reagents of the present invention are suitable for use in any of these known methods. In one aspect, the present invention provides reagents for the magnetic enrichment or separation of leukocytes. The reagents may comprise a magnetically sensitive particle conjugated to phosphorothioate oligonucleotides (PS-ODN).

In some embodiments the magnetically sensitive particle or capture reagent may be conjugated directly to the PS-ODN or, preferably, conjugated to the PS-ODN through a linker. In one aspect, the present invention provides methods of magnetically enriching leukocytes, comprising the steps of adding PS-ODN-conjugated magnetic particles of this invention to a fluid containing leukocytes under conditions such that the PS-ODN conjugated magnetic particles become bound to leukocytes, and applying a magnetic field to localized magnetically labeled leukocytes.

Preferably, the magnetically labeled or captured leukocytes are separated from the fluid for further analysis or use. In some embodiments further analysis or use of the concentrated or captured cells may comprise binding the concentrated or separated cells to any known luecocyte immunoconjugates such as granulocyte, monocyte, or lymphocyte (e.g. anti-CD 19, anti-CD56, anti-CD 19, anti-CD 20, anti-CD 8, anti-CD 4, anti-CD 33, anti-CD 45 etc). The methods of this invention beneficially provide for concentrating or separating leukocytes while preserving antigenic specificity to markers of interest.

Phosphorothioate Oligonucleotides (PS-ODN)

Phosphorothioate oligonucleotides (PS-ODN) and their synthesis have been described in the literature. For example, see U.S. Pat. Nos. 5,644,048 and 5,571,902, and Jahrsdorfer et al., 2005, J. Immun Method. 297: 259-263. each incorporated herein by reference. The synthesis methods described in these references are suitable for use in generating the PS-ODN of the present invention.

PS-ODN molecules of any length may be suitable for use as detection or capture reagents in the present invention. Preferably the length may be are between 15 and 30, more preferably between 15 and 25, nucleotides in length. Earlier studies on different PS-ODN sequences (Table 1) suggested that sequence specificity is not a determining factor or prerequisite for binding to white blood cells, thus any sequence of any length PS-ODN may be incorporated in the methods and reagents of this invention. The PS-ODN reagents of this invention may have one or more phosphorothioate linkages in combination with one or more conventional phosphate linkages. In a preferred embodiment, the PS-ODN comprises a sequence selected from ODN#1, ODN#2, ODN#3, ODN#4, and ODN#5, shown in Table 1, below. In more preferred embodiments, the PS-ODN is selected from ODN#1, ODN#2, ODN#3, ODN#4, and ODN#5, shown in Table 1, below. More preferably, the PS-ODN is either ODN#2 or ODN#5.

TABLE 1

The asterisk (*) indicates phosphorothioate bond between nucleotides.

| | |
|---|---|
| ODN#1 | (SEQ ID NO: 1) |
| T*C*G*T*C*G*T*T*T*T*G*T*C*G*T*T*T*T*G*T*C*G*T*T | |
| ODN#2 | (SEQ ID NO: 2) |
| T*G*C*T*G*C*T*T*T*T*G*T*G*C*T*T*T*T*G*T*G*C*T*T | |
| ODN#3 | (SEQ ID NO: 3) |
| G*G*G*G*G*A*C*G*A*T*C*G*T*C*G*G*G*G*G*G | |
| ODN#4 | (SEQ ID NO: 4) |
| G*G*G*G*G*A*G*C*A*T*G*C*T*G*G*G*G*G*G*G | |
| ODN#5 | (SEQ ID NO: 5) |
| T*C*G*T*C*G*T*T*T*T*C*G*G*C*G*C*G*C*G*C*C*C | |

Not to be bound by theory, the data suggest that PS-ODN bind to carbohydrates and proteins on the cell surface in a non-specific manner, and that the presence of thiol in the phosphodiester backbone of the PS-ODN is involved in the non-specific binding to cell surface. Comparisons of different PS-ODN sequences (Table 1) suggest that sequence specificity is not a determining factor or pre-requisite for binding to white blood cells. As described in the examples, below, PS-ODNs labeled with fluorescein bind to total white blood cells, including lymphocytes, monocytes and granulocytes, indiscriminately. Use of PS-ODN labeled at the 5' end or at cytosine bases provided equivalent results, which indicates that neither the 5' end nor the cytosine bases are not critical for binding of PS-ODN to the cell surface of white blood cells.

Detection Reagents

The fluorescent detection reagents of the present invention comprise PS-ODN conjugated to a detectable label, such as a fluorescent dye (fluorophore). Fluorescent dyes (fluorophores) suitable for use in the present invention can be selected from any of the many dyes suitable for use in biological assays, including flow cytometry and imaging applications. However, the invention is not limited to the use of fluorescent dyes, and any of the detection reagents useful in an optical analysis method that bind to the analyte of interest and enable optical detection, such as nanoparticles detectable by surface-enhanced Raman scattering (SERS), may be used.

Figure 1:
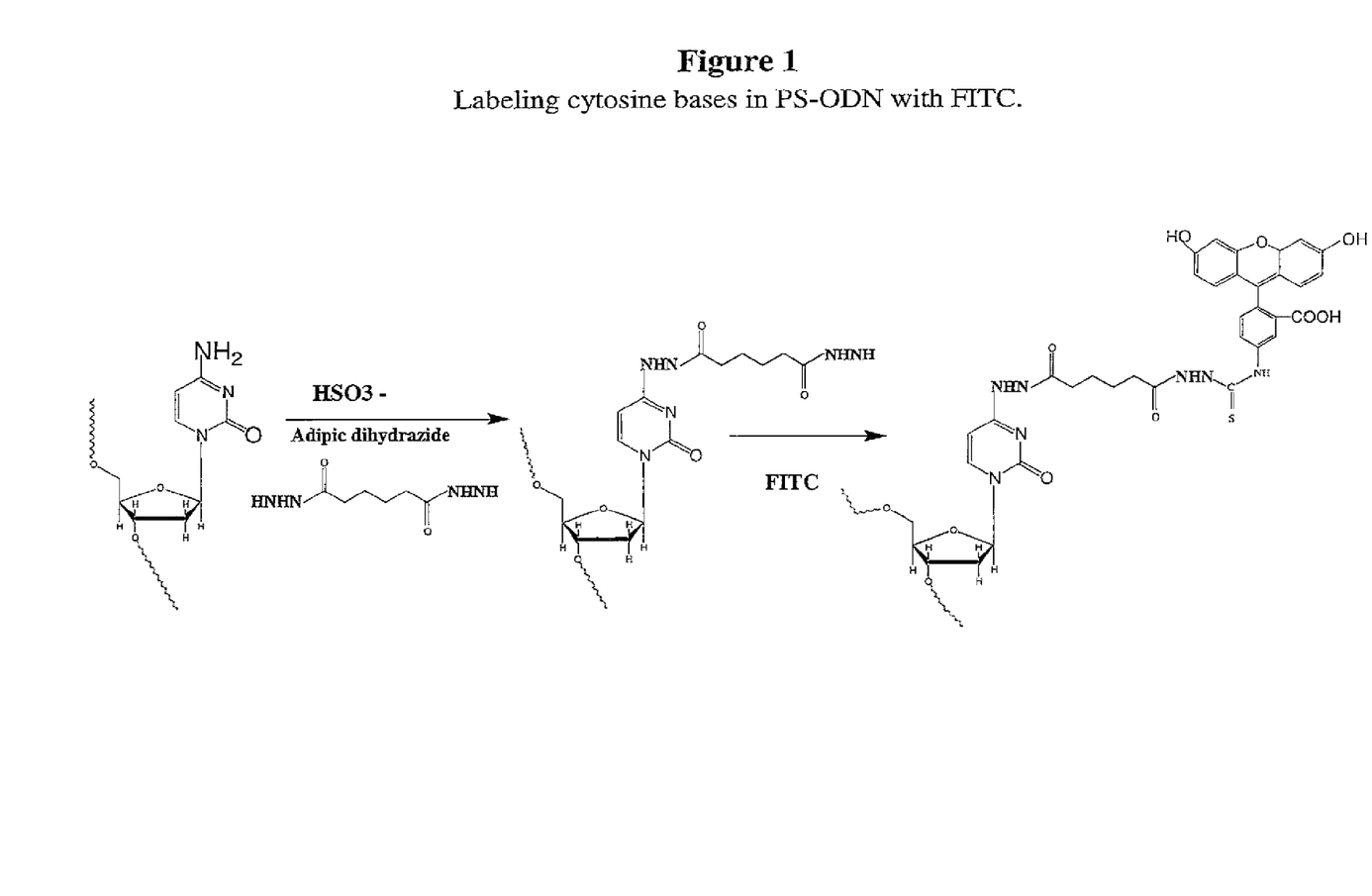
FIG. 1 shows schematically a method for the modification and labeling of cytosine bases in PS-ODN with FITC.
Figure 2:
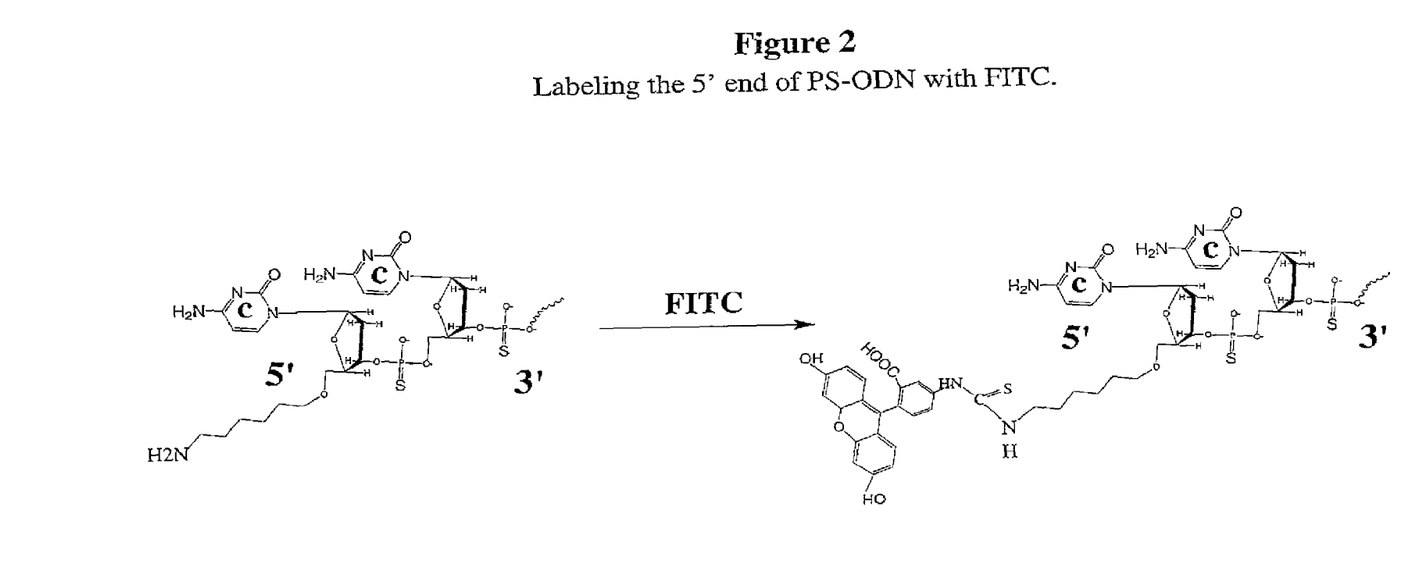
FIG. 2 shows schematically a reaction for the modification and labeling of the 5' end of PSODN with FITC.

Fluorescent dyes are known to those of skill in the art and are commercially available from a number of sources. Suitable fluorescent dyes include, but are not limited to, phycoerythrin ("PE"), fluorescein isothiocyanate ("FITC"), allophycocyanin ("APC"), Texas Red ("TR", Molecular Probes, Inc.), peridinin chlorophyll complex ("PerCp"), CY5 (Biological Detection System) and conjugates thereof coupled to PE (e.g., PE/CY5, PE/APC and PE/TR); etc. A large number of dyes are commercially available from a variety of sources, such as, for example, Molecular Probes (Eugene, Ore.) and Exciton (Dayton, Ohio). Detection reagents can be conjugated to PS-ODN using any of a number of well-known methods of conjugating labels to oligonucleotides. Two preferred conjugation reactions are shown in FIGS. 1 and 2.

Capture Reagents

Capture reagents of the present invention comprise a phosphorothioate oligonucleotide (PSODN) conjugated to a solid surface, or capable of being bound to a solid surface. A wide range of solid surfaces can be used in the present invention, including, for example, beads, plates, slides, columns, microfluidic channels, etc. The solid surface may be conjugated directly to the PS-ODN or, preferably, is conjugated to the PS-ODN through a linker.

Methods of conjugating nucleic acids to a solid surface are well known in the art. Alternatively, PS-ODN may be bound to one member of a binding pair, and the solid surface bound to the other member of the binding pair, such that the binding of the PS-ODN to the solid surface can be carried out after the binding of the PS-ODN to the cell. Examples of binding pairs that are suitable for binding the PS-ODN to the solid surface are well known in the art and include, for example, and antibody and its target antigen pairs, and streptavidin and biotin.

Magnet Capture Reagent

The magnetic capture reagents of the present invention are magnetic particles bound to PSODN. As used herein, "magnetic particles" refers to any particle that contains a magnetic or magnetically responsive material. Magnetic particles can be of any shape, but typically are approximately spherical ("microspheres"). Magnetic particles suitable for use in the present invention preferably have a diameter in the nanometer to micrometer range, typically about 0.01 to 50 µm in diameter, preferably about 0.1 to 10 µm, more preferably about 0.2 to 0.4 Rm. Preferably, the magnetic particles are paramagnetic or superparamagnetic. Magnetic particles suitable for use in the present invention are commercially available from a number of sources, including, but not limited to, BD Biosciences (San Jose, Calif.), Invitrogen (Carlsbad, Calif.), Miltenyi Biotech (Bergisch Gladbach, Germany), and Polysciences (Warrington, Pa.). In general, magnetic particles sold for use in cell separation assays are suitable for use in the present invention. Conjugation of the magnetic particles to PS-ODN can be carried using any of a number of well-known methods of conjugating oligonucleotides to magnetic particles. Magnetic particles are commercially available with reactive surface groups suitable for use in conjugating to oligonucleotides. Alternatively, as with other solid surfaces, the PS-ODN may be bound to one member of a binding pair, and the magnetic particle bound to the other member of the binding pair, such that the binding of the PS-ODN to the magnetic particle can be carried out after the binding of the PS-ODN to the cell.

EXAMPLES

The following examples are put forth so as to provide those of ordinary skill in the art with a complete disclosure and

Example 1

PS-ODN#2 Binding to Total White Blood Cells

Figure 3:
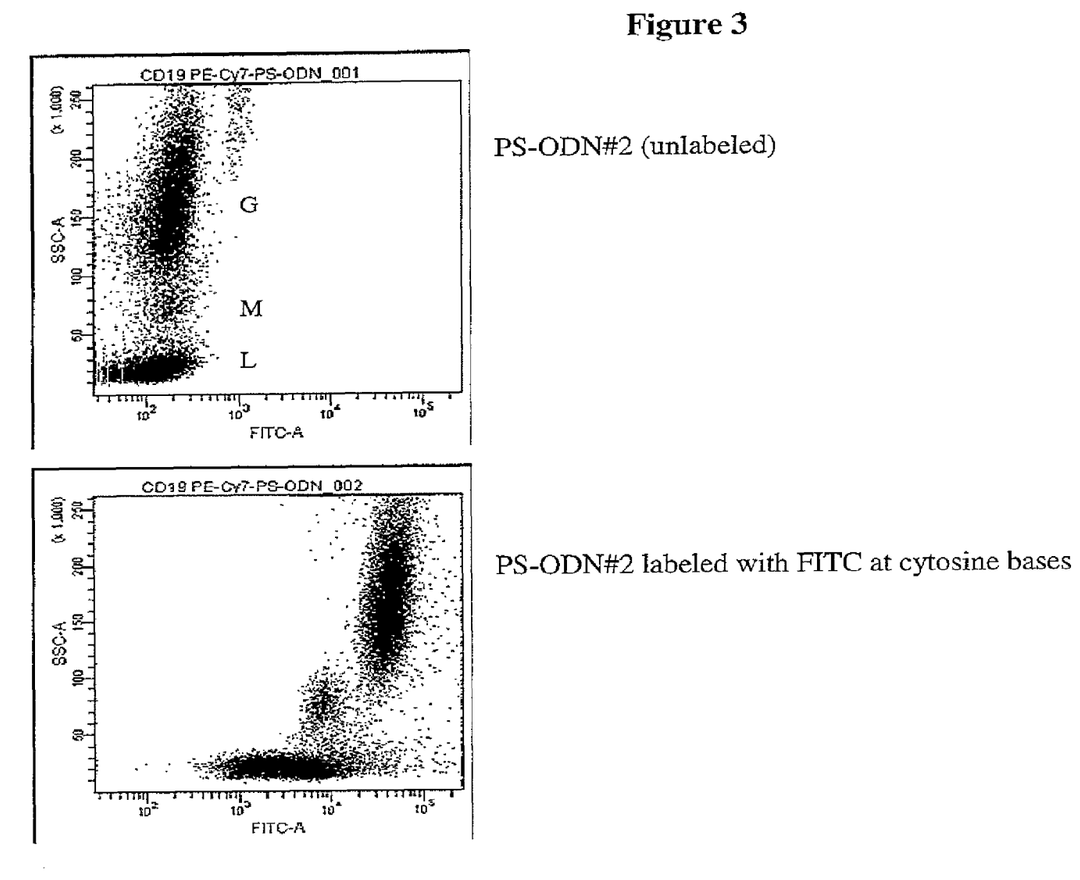
FIG. 3 shows data demonstrating the binding of PS-ODN#2 to total white blood cells. Leukocyte subpopulations of granulocytes, monocytes, and lymphocytes are labeled as G, M and L, respectively.

PS-ODN#2 labeled with FITC, conjugated to cytosine residues, were synthesized as shown in FIG. 1. 50-μl blood samples were incubated with either 5 μg unlabeled PS-ODN#5 or FITC-PS-ODN#2 for 30 minutes, followed by treatment with BD FACS™ Lysing Solution. Cells were centrifuged, washed, and analyzed on a flow cytometer. The data are shown in FIG. 3.

The results show that PS-ODN#2 labeled with FITC bind to all three populations of white blood cells (lymphocytes, monocytes and granulocytes), i.e., all white blood cells. The results further show that PS-ODN can be labeled with FITC at 5' end or at cytosine bases (FIGS. 1 and 2). These modifications (FITC-labeling) either at 5' end or at cytosine bases do not abolish the ability of PS-ODN to bind to cell surface (shown in FIGS. 3 and 4) where the labeled PS-ODNs bind to all three populations of white blood cells.

Example 2

PS-ODN#5 Binding to Total White Blood Cells

Figure 4:
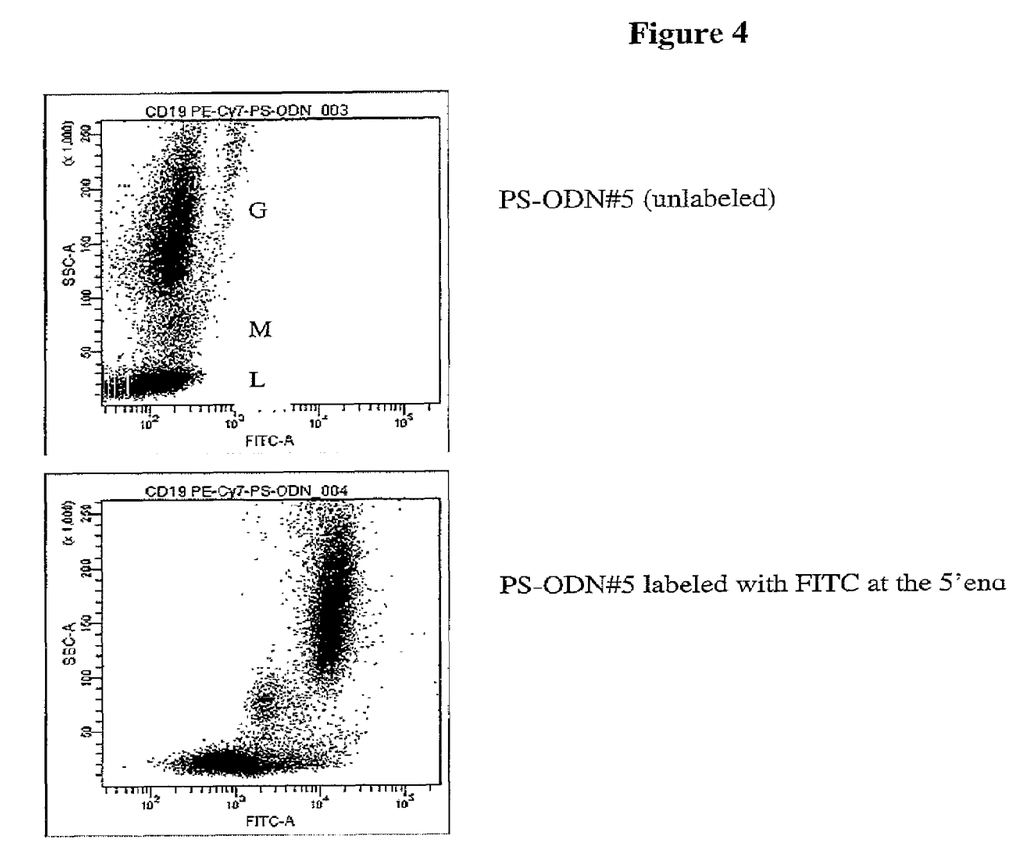

PS-ODN#5 labeled with FITC at the 5'-end were synthesized as shown in FIG. 2. 50-μl blood samples were incubated with either 5 μg unlabeled PS-ODN#5 or FITC-PS-ODN#5 for 30 minutes, followed by treatment with BD FACS™ Lysing Solution. Cells were centrifuged, washed, and analyzed on a flow cytometer. The data are shown in FIG. 4. The results show that PS-ODN#5 labeled with FITC bind to all three populations of white blood cells (lymphocytes, monocytes and granulocytes), i.e., all white blood cells. The results further show that PS-ODN can be labeled with FITC at 5' end or at cytosine bases (FIGS. 1 and 2). These modifications (FITC-labeling) either at 5' end or at cytosine bases do not abolish the ability of PS-ODN to bind to cell surface (shown in FIGS. 3 and 4) where the labeled PS-ODNs bind to all three populations of white blood cells.

Example 3

Staining Cells with FITC-PS-ODN#2 and CD19-PE-Cy7

Figure 5:
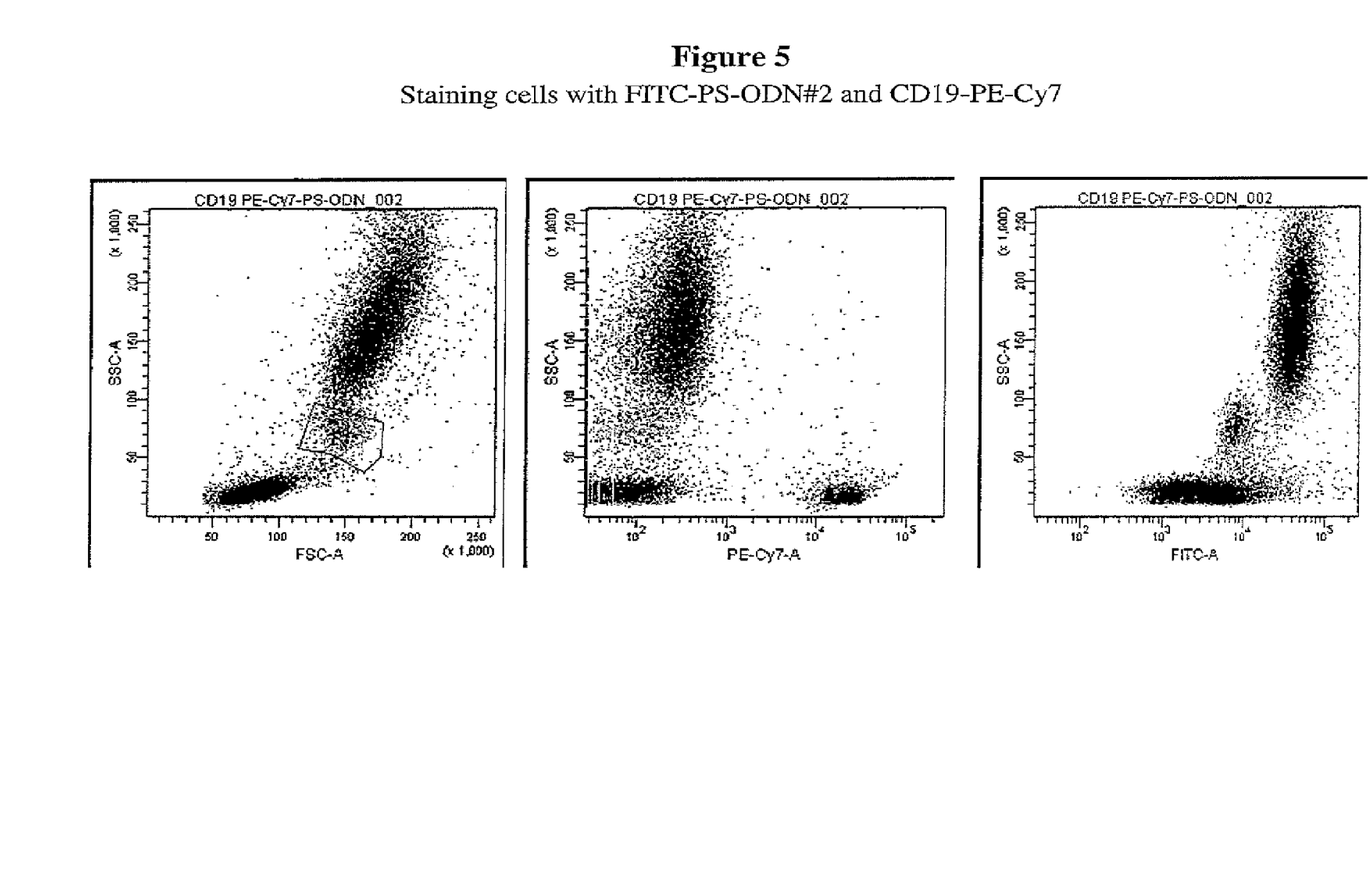
FIG. 5 shows data from an analysis of cells stained with FITC-PS-ODN#2 and CD19-PE-Cy7.

A 50-μl blood sample was incubated with 5 μg FITC-PS-ODN#2 and 150 ng anti-CD19-PECy7 for 30 minutes, followed by treatment with BD FACS™ Lysing Solution. Cells were centrifuged, washed, and analyzed on a flow cytometer. The data are shown in FIG. 5. The data indicate that the labeled PS-ODN binds to all white blood cells. Furthermore, the binding of the labeled PS-ODN does not mask the specific antigen on the cell surface, as shown by the staining of the cells using labeled CD 19-specific antibody. Thus, binding of PS-ODNs to the cell surface provides a method of staining cells that maintains the antigenic integrity of the cells.

Example 4

Staining Cells with FITC-PS-ODN#5 and CD19-PE-Cy7

Figure 6:
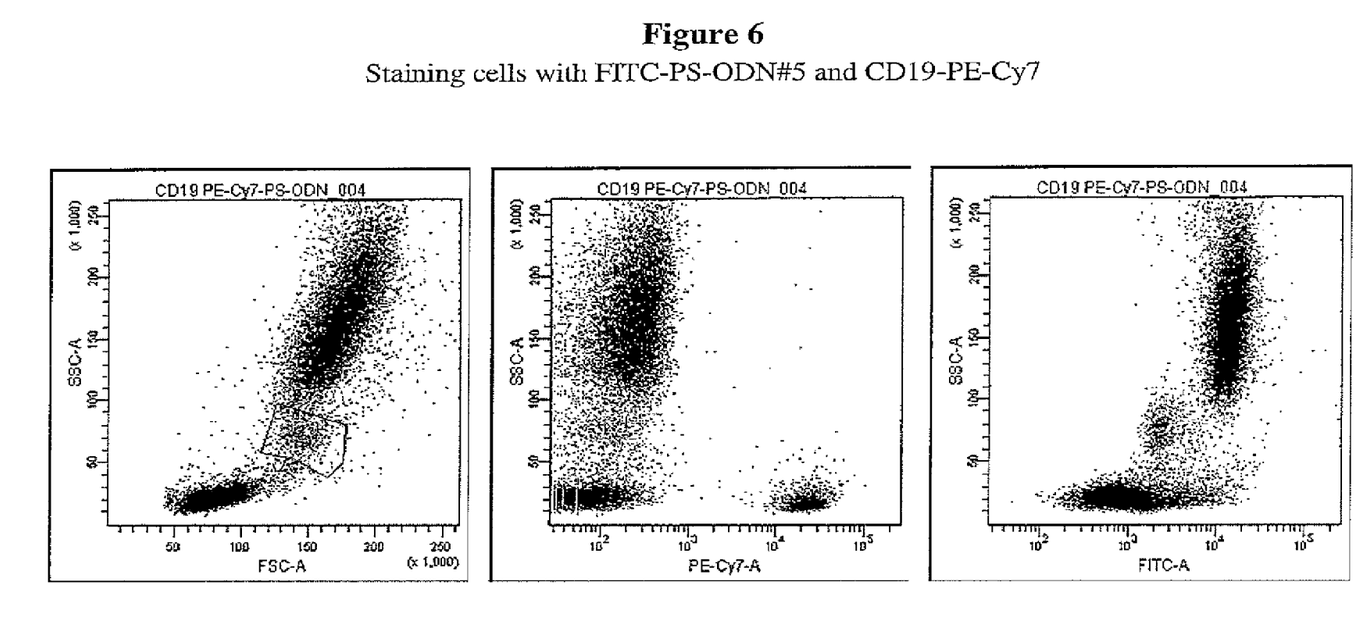
FIG. 6 shows data from an analysis of cells stained with FITC-PS-ODN#5 and CD19-PE-Cy7.

A 50-μl blood sample was incubated with 5 μg FITC-PS-ODN#5 and 150 ng anti-CD19-PE5 Cy7 for 30 minutes, followed by treatment with BD FACS™ Lysing Solution. Cells were centrifuged, washed, and analyzed on a flow cytometer. The data are shown in FIG. 6. The data indicate that the labeled PS-ODN binds to all white blood cells. Furthermore, the binding of the labeled PS-ODN does not mask the specific antigen on the cell surface, as shown by the staining of the cells using labeled CD 19-specific antibody.

Example 5

Magnetic Separation of Total White Blood Cells with PS-ODN-IMag

Magnetic particles (BD IMag magnetic particles, BD Biosciences, San Jose, Calif.) were conjugated to PS-ODN#5. A 50-μl sample of whole blood was incubated with 32 μg Fe of PS-ODN#5-conjugated magnetic particles for 30 minutes, followed by treatment with BD FACS™ Lysing Solution. Cells were magnetically separated using a BD IMagnet™ cell separation magnet (BD Biosciences, San Jose, Calif.), washed, and analyzed on a flow cytometer. As a control, a sample of untreated cells was analyzed by flow cytometer. The data are presented in FIG. 7.

Figure 7:
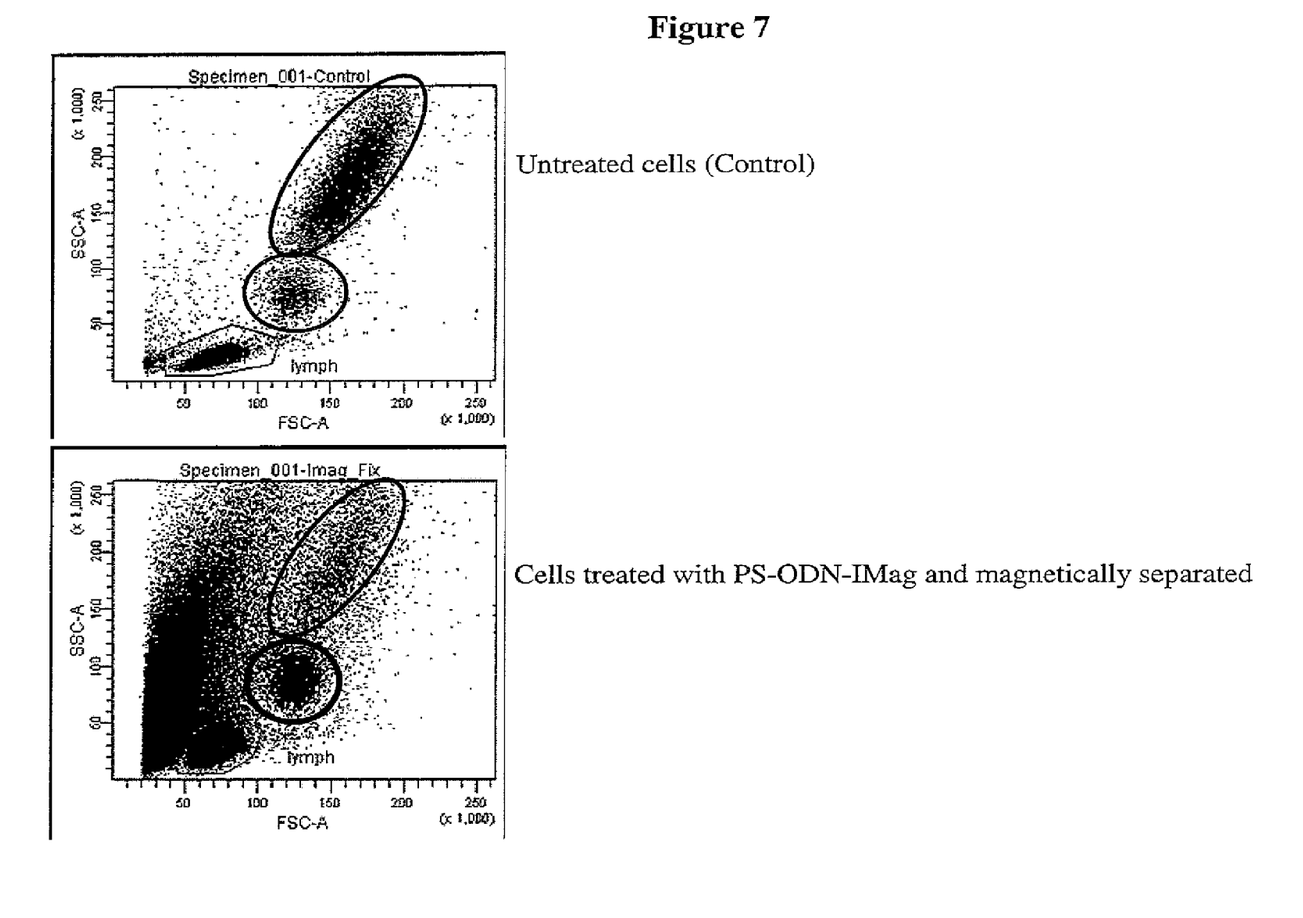
FIG. 7 shows data demonstrating the magnetic enrichment of white blood cells from a sample of whole blood using PS-ODN-IMag particles and magnetic separation.

The results show that PS-ODN-conjugated magnetic particles may be used to enrich or separate white blood cells by any separation method, (e.g., magnetic separation). An advantage of the present methods is that the cell surface markers are left intact for antibody labeling and analysis.

---

We claim:

1. A method for indiscriminately labeling lymphocytes, monocytes and granulocytes in a fluid sample containing leukocytes, the method comprising:
    adding a labeling reagent conjugated phosphorothioate oligonucleotide (PS-ODN) that indiscriminately binds to lymphocytes, monocytes and granulocytes to said fluid sample containing leukocytes under conditions such that the labeling reagent conjugated phosphorothioate oligonucleotide becomes bound to the lymphocytes, monocytes and granulocytes to indiscriminately label the lymphocytes, monocytes and granulocytes in the fluid sample with the labeling reagent; and
    (a) identifying leukocytes bound by the labeling reagent conjugated phosphorothioate oligonucleotide as lymphocytes, monocytes and granulocytes; or
    (b) concentrating leukocytes bound by the labeling reagent conjugated phosphorothioate oligonucleotide to separate lymphocytes, monocytes and granulocytes from the fluid sample.

2. The method of claim 1 further comprising adding an immuno-conjugate to the fluid under conditions such that the immune-conjugate becomes bound to the labeled leukocytes.

3. The method of claim 2, wherein the labeling reagent conjugated phosphorothioate oligonucleotide is conjugated to a magnetic capture reagent.

4. The method of claim 1, wherein the labeling reagent conjugated phosphorothioate oligonucleotide is conjugated to a fluorescent dye.

5. The method of claim 4, further comprising adding an immuno-conjugate to the fluid under conditions such that the immune-conjugate becomes bound to the labeled leukocytes.

6. The method of claim 1, wherein the labeling reagent conjugated phosphorothioate oligonucleotide is conjugated to a capture reagent.

7. The method of claim 6, wherein the capture reagent is magnetic.

8. The method of claim 7, further comprising placing the fluid in a magnetic field such that leukocytes bound to the magnetic capture reagents are concentrated.

9. The method of claim 8, further comprising adding an immuno-conjugate to the concentrated leukocytes under conditions such that the immune-conjugate becomes bound to the labeled leukocytes.

10. The method of claim 8, wherein the immuno-conjugate is an anti-CD19 antibody.

11. The method of claim 1, wherein said PS-ODN is between 15 and 25 nucleotides in length.

12. The method of claim 1, wherein said PS-ODN comprises a sequence selected from the PS-ODN consisting of ODN#1 (SEQ ID NO:1), ODN#2 (SEQ ID NO:2), ODN#3 (SEQ ID NO:3), ODN#4 (SEQ ID NO:4), and ODN#5 (SEQ ID NO:5).

13. A phosphorothioate oligonucleotide (PS-ODN) that indiscriminately binds to lymphocytes, monocytes and granulocytes and is conjugated to a detectable label.

14. The PS-ODN of claim 13, wherein the detectable label is a fluorescent dye.

15. The PS-ODN of claim 13, wherein the PS-ODN is between 15 and 25 nucleotides in length.

16. The PS-ODN of claim 13, wherein the PS-ODN comprises a sequence selected from the PS-ODN consisting of ODN#1 (SEQ ID NO:1), ODN#2 (SEQ ID NO:2), ODN#3 (SEQ ID NO:3), ODN#4 (SEQ ID NO:4), and ODN#5 (SEQ ID NO:5).

17. The PS-ODN of claim 16, wherein the PS-ODN is either ODN#2 (SEQ ID NO:2) or ODN#5 (SEQ ID NO:5).

18. A magnetic capture reagent for labeling leukocytes, comprising a magnetic particle conjugated to a phosphorothioate oligonucleotide (PS-ODN) that indiscriminately binds to lymphocytes, monocytes and granulocytes.

19. The magnetic capture reagent of claim 18, wherein the PS-ODN is between 15 and 25 nucleotides in length.

20. The magnetic capture reagent of claim 19, wherein the PS-ODN comprises a sequence selected from the PS-ODN consisting of ODN#1 (SEQ ID NO:1), ODN#2 (SEQ ID NO:2), ODN#3 (SEQ ID NO:3), ODN#4 (SEQ ID NO:4), and ODN#5 (SEQ ID NO:5).

* * * * *